US012661140B2

(12) United States Patent (10) Patent No.: US 12,661,140 B2
Matsuki et al. (45) Date of Patent: Jun. 23, 2026

(54) TREATMENT SYSTEM, CONTROL DEVICE, CONTROL METHOD, IMAGE DETERMINATION APPARATUS, AND IMAGE DETERMINATION METHOD

(71) Applicant: OLYMPUS CORPORATION, Hachioji (JP)

(72) Inventors: Kenji Matsuki, Hachioji (JP); Yuto Hirabayashi, Suwa (JP); Shunsuke Matsui, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 946 days.

(21) Appl. No.: 17/860,817

(22) Filed: Jul. 8, 2022

(65) Prior Publication Data

US 2022/0338898 A1     Oct. 27, 2022

Related U.S. Application Data

(63) Continuation of application No. PCT/JP2020/000496, filed on Jan. 9, 2020.

(51) Int. Cl.
*A61B 17/32*          (2006.01)
*A61B 1/00*           (2006.01)
(Continued)

(52) U.S. Cl.
CPC ..... *A61B 17/320092* (2013.01); *G16H 20/40* (2018.01); *A61B 1/00006* (2013.01);
(Continued)

(58) Field of Classification Search
CPC ................... G16H 20/40; G16H 30/40; A61B 2017/00123; A61B 2017/320094;
(Continued)

(56) References Cited

U.S. PATENT DOCUMENTS

2004/0097915 A1     5/2004  Refior et al.
2006/0020261 A1     1/2006  Refior et al.
(Continued)

FOREIGN PATENT DOCUMENTS

CN          106477417 A       3/2017
JP          2006-506172 A     2/2006
(Continued)

OTHER PUBLICATIONS

Feb. 25, 2020 International Search Report issued in International Patent Application No. PCT/JP2020/000496.

*Primary Examiner* — Jason E Flick
(74) *Attorney, Agent, or Firm* — Oliff PLC

(57) ABSTRACT

A treatment system includes a treatment tool, an imaging apparatus, and a control device. The treatment tool is configured to perform treatment on a living tissue by applying treatment energy from an end effector to the living tissue based on supplied electric power. The imaging apparatus captures an image of the living tissue in a state in which the treatment energy is applied from the end effector to the living tissue. The control device includes a processor to control the imaging apparatus by acquiring the captured image, determining whether an abnormality has occurred in the end effector based on the acquired captured image, and executing an instruction to stop supply of the electric power to the treatment tool when determining that the abnormality has occurred in the end effector.

16 Claims, 11 Drawing Sheets

(51) Int. Cl.
  *A61B 17/00* (2006.01)
  *A61B 18/00* (2006.01)
  *G16H 20/40* (2018.01)
(52) U.S. Cl.
  CPC .................. *A61B 1/000096* (2022.02); *A61B 2017/00057* (2013.01); *A61B 2017/00123* (2013.01); *A61B 2017/320094* (2017.08)
(58) Field of Classification Search
  CPC ........ A61B 90/361; A61B 2018/00589; A61B 2018/00601; A61B 2018/00607; A61B 17/320068; A61B 18/04; A61B 18/12; A61B 18/1206; A61B 18/14; A61B 18/1442; A61B 18/1445; A61B 18/082; A61B 18/085; A61B 17/32; A61B 2017/320069; A61B 2017/320078; A61B 17/320092; A61B 2017/320093; A61B 2017/320095; A61B 2017/320082; A61B 2018/00708; A61B 2018/00982
  See application file for complete search history.

(56) References Cited

U.S. PATENT DOCUMENTS

| | | | |
|---|---|---|---|
| 2009/0259244 A1 | 10/2009 | Shimizu | |
| 2013/0211244 A1* | 8/2013 | Nathaniel | A61B 34/20 |
| | | | 600/424 |
| 2017/0284860 A1* | 10/2017 | Dickerson | A61B 5/00 |
| 2019/0046262 A1* | 2/2019 | Hayashida | A61B 18/18 |
| 2020/0246033 A1* | 8/2020 | Burkhard | A61B 90/361 |

FOREIGN PATENT DOCUMENTS

| | | |
|---|---|---|
| JP | 2006-325940 A | 12/2006 |
| JP | 2009-240757 A | 10/2009 |
| JP | 2009-254821 A | 11/2009 |
| JP | 2010-268961 A | 12/2010 |
| JP | 4813097 B2 | 11/2011 |
| WO | 2017/187523 A1 | 11/2017 |

* cited by examiner

F1

LT    42    421    Ar1    423
      (40)

F2

LT    42    421    Ar2    423
      (40)

LT      42      421      Ar2      423
        (40)

MATCH RATE OF
OUTER SHAPE

Th1

TIME

FIG.7

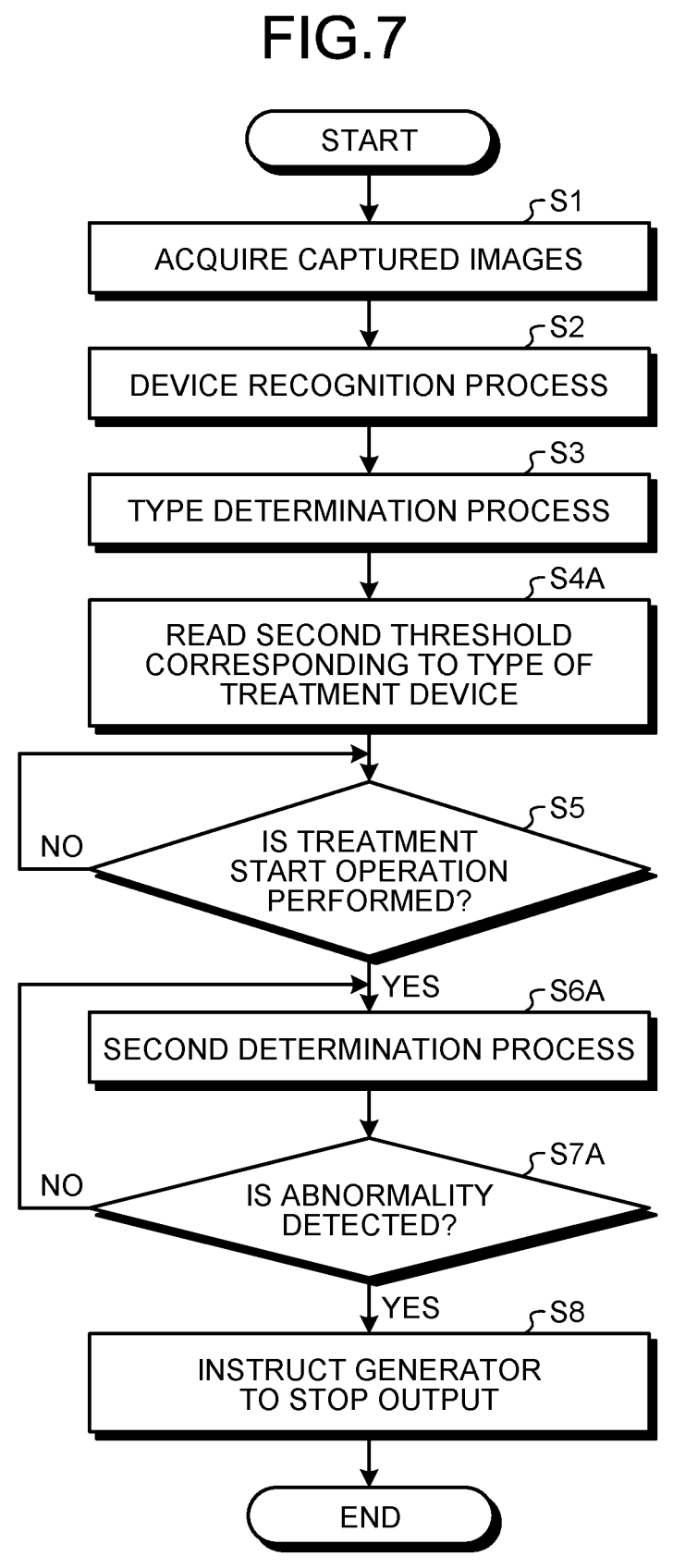

START

S1
ACQUIRE CAPTURED IMAGES

S2
DEVICE RECOGNITION PROCESS

S3
TYPE DETERMINATION PROCESS

S4A
READ SECOND THRESHOLD
CORRESPONDING TO TYPE OF
TREATMENT DEVICE

S5
IS TREATMENT
START OPERATION
PERFORMED?          NO

YES

S6A
SECOND DETERMINATION PROCESS

S7A
IS ABNORMALITY
DETECTED?          NO

YES

S8
INSTRUCT GENERATOR
TO STOP OUTPUT

END

TREATMENT SYSTEM, CONTROL DEVICE, CONTROL METHOD, IMAGE DETERMINATION APPARATUS, AND IMAGE DETERMINATION METHOD

CROSS-REFERENCE TO RELATED APPLICATION

This application is a continuation of International Application No. PCT/JP2020/000496, filed on Jan. 9, 2020, the entire contents of which are incorporated herein by reference.

BACKGROUND

1. Technical Field

The present disclosure relates to a treatment system, a control device, a control method, an image determination apparatus, and an image determination method.

2. Related Art

In the related art, a treatment system that includes a treatment tool for performing treatment on a living tissue by applying treatment energy to the living tissue from an end effector in accordance with supplied electric power, and a generator that supplies the electric power to the treatment tool has been known.

In the treatment tool of the related art, ultrasound energy is adopted as the treatment energy. Specifically, the treatment tool includes an ultrasound transducer that generates ultrasound vibration in accordance with the electric power supplied from the generator. Further, an end effector of the treatment tool includes a vibration transmission member that transmits the ultrasound vibration, and applies the transmitted ultrasound vibration to a living tissue. Furthermore, the generator of the related art detects an abnormality (bend or falling off after bend) of the end effector, and displays information indicating occurrence of the abnormality on a display unit.

SUMMARY

In some embodiments, a treatment system includes a treatment tool configured to perform treatment on a living tissue by applying treatment energy from an end effector to the living tissue in accordance with supplied electric power; an imaging apparatus configured to capture an image of the living tissue in a state in which the treatment energy is applied from the end effector to the living tissue; and a control device including a processor configured to control operation of the imaging apparatus, the processor being configured to: allow an instruction to control supply of the electric power to the treatment tool, acquire the captured image from the imaging apparatus, determine whether an abnormality has occurred in the end effector based on the acquired captured image, and execute an instruction to stop the supply of the electric power to the treatment tool in response to determining that the abnormality has occurred in the end effector.

In some embodiments, a control device including a processor configured to control operation of an imaging apparatus, the processor communicating with a treatment tool performing treatment on a living tissue by applying treatment energy from an end effector to the living tissue in accordance with supplied electric power, the processor being configured to: allow an instruction to control supply of the electric power to the treatment tool, acquire a captured image that is obtained by the imaging apparatus that captures the image of the living tissue in a state in which the treatment energy is applied to the living tissue from the end effector, determine whether an abnormality has occurred in the end effector based on the acquired captured image, and execute an instruction to stop the supply of the electric power to the treatment tool in response to determining that the abnormality has occurred in the end effector.

In some embodiments, provided is a control method implemented by a processor of a control device, the control method comprising: acquiring a captured image that is obtained by an imaging apparatus that captures the image of the living tissue in a state in which treatment energy is applied from an end effector to a living tissue; determining whether an abnormality has occurred in the end effector based on the acquired captured image; and executing an instruction to stop supply of electric power to the treatment tool in response to determining that the abnormality has occurred in the end effector.

In some embodiments, an image determination apparatus comprising: a processor comprising hardware, the processor being configured to: allow an instruction to control supply of electric power to a treatment tool, acquire a captured image that is obtained by an imaging apparatus that captures the image of living tissue in a state in which treatment energy is applied from an end effector of the treatment tool to the living tissue, and determine whether an abnormality has occurred in the end effector based on the acquired captured image.

In some embodiments, an image determination method comprising: controlling supply of electric power to a treatment tool; acquiring a captured image that is obtained by an imaging apparatus that captures the image of living tissue in a state in which treatment energy is applied from an end effector of the treatment tool to the living tissue; and determining whether an abnormality has occurred in the end effector based on the captured image.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 7 is a flowchart illustrating a control method according to a second embodiment;

DETAILED DESCRIPTION

Modes (hereinafter, embodiments) for carrying out the disclosure will be described below with reference to the drawings. The disclosure is not limited by the embodiments described below. In addition, in description of the drawings, the same components are denoted by the same reference symbols.

First Embodiment

Overall Configuration of Treatment System

Figure 1:
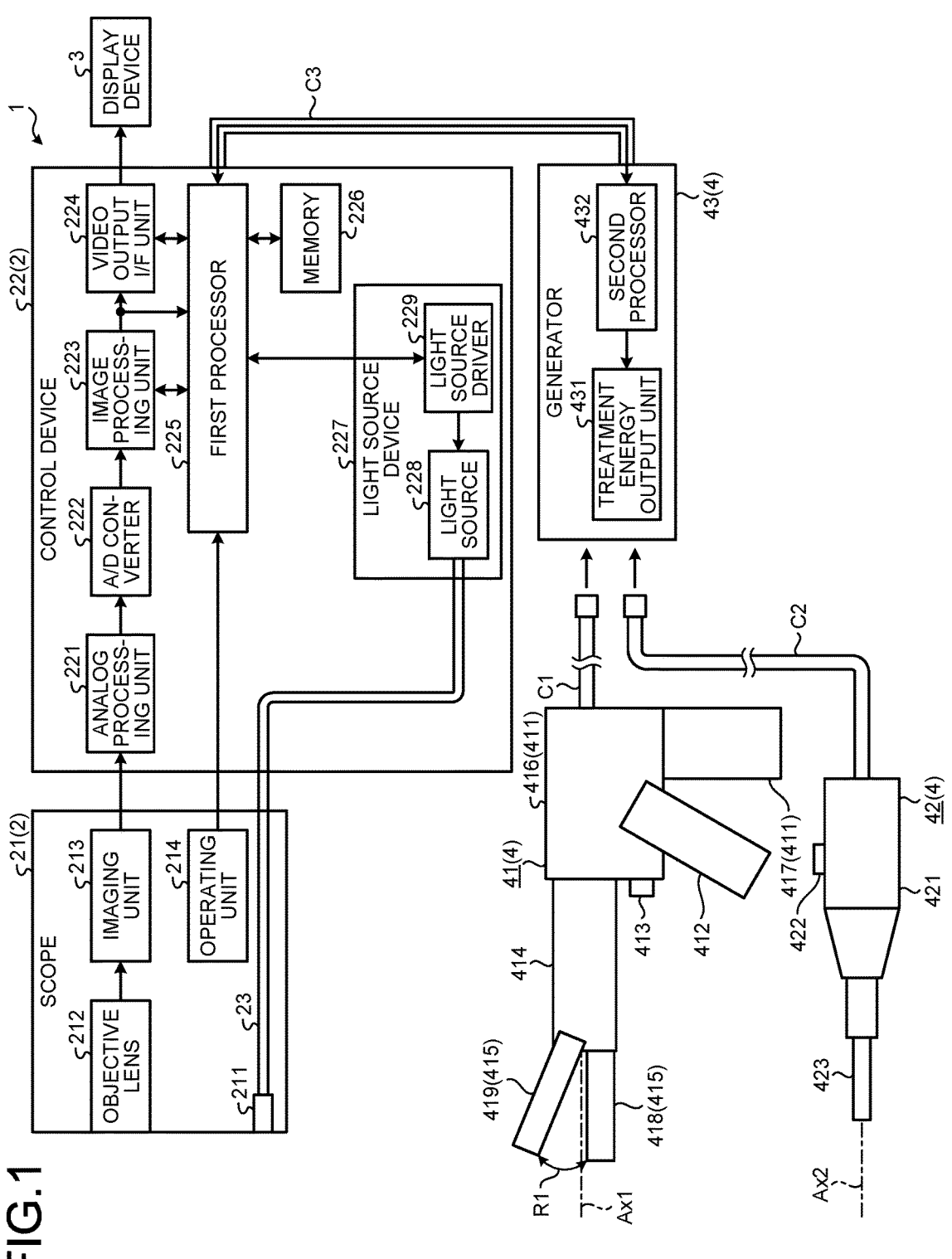
FIG. 1 is a diagram illustrating a treatment system according to a first embodiment.

FIG. 1 is a diagram illustrating a treatment system 1 according to a first embodiment.

The treatment system 1 is a system that performs treatment on a living tissue that is a target for treatment (hereinafter, described as a target region) inside a living body while observing the inside of the living body. The treatment system 1 includes, as illustrated in FIG. 1, an endoscope device 2, a display device 3, and a therapy device 4.

Configurations of the endoscope device 2 and the therapy device 4 will be described below in sequence.

Configuration of Endoscope Device

The endoscope device 2 is a device that observes an inside of a living body. As illustrated in FIG. 1, the endoscope device 2 includes a scope 21 and a control device 22.

The scope 21 corresponds to an imaging apparatus. The scope 21 is inserted into a living body and captures an image of the inside of the living body. In the first embodiment, the scope 21 is configured with a flexible endoscope that is flexible, that has a thin and elongated shape, and that is inserted into the living body. Further, the scope 21 is connected to the control device 22 by a connector (not illustrated) in a detachably attachable manner. As illustrated in FIG. 1, the scope 21 includes an illumination lens 211, an objective lens 212, an imaging unit 213, and an operating unit 214.

The illumination lens 211 is arranged at a distal end of the scope 21 so as to face an emission end of a light guide 23 (FIG. 1). Further, light emitted from the light guide 23 passes through the illumination lens 211 and is applied to the inside of the living body.

The objective lens 212 is arranged at the distal end of the scope 21. Further, the objective lens 212 captures light (object image) that is applied from the illumination lens 211 to the inside of the living body and that is reflected inside the living body, and forms an image on a light receiving surface of the imaging unit 213.

The imaging unit 213 captures the object image that is formed by the objective lens 212 and generates a captured image under the control of the control device 22. Further, the imaging unit 213 outputs the generated captured image to the control device 22.

The operating unit 214 includes various switches (not illustrated) for receiving user operation performed by a user, such as a doctor. Further, the operating unit 214 outputs an operation signal corresponding to the operation to the control device 22.

The control device 22 includes a central processing unit (CPU), a field-programmable gate array (FPGA), or the like, and comprehensively controls operation of the scope 21 and the display device 3. As illustrated in FIG. 1, the control device 22 includes an analog processing unit 221, an analog-to-digital (A/D) converter 222, an image processing unit 223, a video output interface (I/F) unit 224, a first processor 225, a memory 226, and a light source device 227.

The analog processing unit 221 receives input of the captured image (analog signal) from the scope 21, and performs analog processing, such as a clamp processing and noise elimination processing (correlated double sampling (CDS)), on the captured image.

The A/D converter 222 performs A/D conversion on the captured image (analog signal) that is subjected to the analog processing, and outputs the converted captured image (digital signal).

The image processing unit 223 performs various kinds of image processing on the input captured image by using various parameters that are used for the image processing and that are stored in the memory 226, under the control of the first processor 225. Examples of the various kinds of image processing include optical black subtraction processing, white balance (WB) adjustment processing, demosaicing processing, color matrix calculation processing, gamma correction processing, color reproduction processing, and edge enhancement processing.

The video output I/F unit 224 is configured with a digital analog converter (DAC), an encoder, or the like, and generates a display video signal on the basis of the captured image (digital signal) that is subjected to the various kinds of image processing by the image processing unit 223. Further, the video output I/F unit 224 outputs the display video signal to the display device 3.

The display device 3 is configured with a display using liquid crystal, organic electro luminescence (EL), or the like. Further, the display device 3 receives input of the display video signal from the video output I/F unit 224, and displays a captured image or the like based on the display video signal.

The light source device 227 includes, as illustrated in FIG. 1, a light source 228 and a light source driver 229. Meanwhile, in the first embodiment, the light source device 227 is incorporated in the control device 22, but the configuration is not limited to this example, and the light source device 227 may be configured independently of the control device 22.

The light source 228 is configured with, for example, a white light emitting diode (LED) or the like, and emits light in accordance with supplied electric power. Further, the light emitted from the light source 228 passes through the light guide 23 and the illumination lens 211 and is applied to the inside of the living body.

The light source driver 229 supplies electric power to the light source 228 under the control of the first processor 225.

The first processor 225 corresponds to a processor. The first processor 225 is configured with, for example, a CPU, an FPGA, or the like, and controls operation of the scope 21, operation of the display device 3, and operation of the entire control device 22. Further, the control device 22 and a generator 43 (FIG. 1) included in the therapy device 4 are connected to each other by a third electrical cable C3 (FIG. 1) in a detachably attachable manner. Furthermore, the first processor 225 controls operation of the generator 43 through the third electrical cable C3. Meanwhile, detailed functions of the first processor 225 will be described in relation to a "control method performed by the first processor" to be described later.

The memory 226 stores therein a program executed by the first processor 225, information needed for the process performed by the first processor 225, various parameters for the image processing as described above, and the like.

Configuration of Therapy Device

The therapy device 4 applies the treatment energy to a target region and performs treatment on the target region. Examples of the treatment include coagulation and incision of the target region. Further, examples of the treatment energy include at least one of ultrasound energy, high-frequency, and thermal energy. Meanwhile, application of the ultrasound energy to the target region indicates that ultrasound vibration is applied to the target region. Furthermore, application of the high-frequency energy to the target region indicates that a high-frequency electric current is caused to flow into the target region. Moreover, application of the thermal energy to the target region indicates that heat generated in a heater or the like is transmitted to the target region. The therapy device 4 includes, as illustrated in FIG. 1, a first treatment device 41, a second treatment device 42, and the generator 43.

Meanwhile, in the therapy device 4, it is possible to select a use mode in which the first treatment device 41 and the generator 43 are connected to each other by a first electrical cable C1 (FIG. 1) or a use mode in which the second treatment device 42 and the generator 43 are connected to each other by a second electrical cable C2 (FIG. 1), depending on a treatment method, a type of the target region, or the like.

The first treatment device 41 corresponds to a treatment tool, and is a clamp-type treatment device that performs treatment on the target region while grasping the target region. As illustrated in FIG. 1, the first treatment device 41 includes a first holding case 411, an operation knob 412, a first switch 413, a shaft 414, and a grasping unit 415.

The first holding case 411 supports the entire first treatment device 41. As illustrated in FIG. 1, the first holding case 411 includes a holding case main body 416 that is located on a central axis Ax1 (FIG. 1) of the shaft 414, and a fixed handle 417 that extends from the holding case main body 416 to a lower side in FIG. 1 and that is grasped by an operator.

The operation knob 412 is supported about an axis so as to be rotatable about the first holding case 411, and receives open-close operation performed by the operator.

The first switch 413 is arranged so as to be exposed to the outside from the first holding case 411, and receives press (hereinafter, described as first treatment start operation) performed by the operator. Further, the first switch 413 outputs, via the first electrical cable C1, an operation signal corresponding to the first treatment start operation to the generator 43.

The shaft 414 has a cylindrical shape and an end portion thereof on a proximal end side (right side in FIG. 1) is connected to the holding case main body 416. Further, the grasping unit 415 is attached to an end portion of the shaft 414 on a distal end side (left side in FIG. 1). Furthermore, in the shaft 414, an open-close mechanism (not illustrated) is arranged that opens and closes a first grasper 418 and a second grasper 419 that are included in the grasping unit, in accordance with the open-close operation that is performed on the operation knob 412 by the operator.

The grasping unit 415 corresponds to an end effector. The grasping unit 415 is a part that performs treatment on the target region while grasping the target region. The grasping unit 415 includes, as illustrated in FIG. 1, the first grasper 418 and the second grasper 419.

The first grasper 418 and the second grasper 419 correspond to a pair of graspers, and are able to grasp the target region by being opened and closed in a direction of arrow R1 (FIG. 1) in accordance with the open-close operation that is performed on the operation knob 412 by the operator. Further, at least one of the first grasper 418 and the second grasper 419 applies the treatment energy to the grasped target region under the control of the generator 43. Accordingly, the target region is subjected to treatment.

The second treatment device 42 corresponds to the treatment tool, and is a non-clamp type treatment device that is not able to grasp the target region and that performs treatment on the target region while coming into contact with the target region. The second treatment device 42 includes, as illustrated in FIG. 1, a second holding case 421, a second switch 422, and an end effector 423.

The second holding case 421 has a substantially cylindrical shape that extends along a central axis Ax2, and supports the end effector 423.

The second switch 422 is arranged so as to be exposed to the outside from the second holding case 421, and receives press (hereinafter, described as second treatment start operation) performed by the operator. Further, the second switch 422 outputs, via the second electrical cable C2, an operation signal corresponding to the second treatment start operation to the generator 43.

The end effector 423 has an elongated shape that extends along the central axis Ax2, and is mounted inside the second holding case 421 such that an end portion on a distal end side (left side in FIG. 1) is exposed to the outside. Further, the end effector 423 applies, in a state in which an end portion on a distal end side comes into contact with the target region, the treatment energy from the end portion to the target region under the control of the generator 43. Accordingly, the target region is subjected to treatment.

The generator 43 includes a CPU, an FPGA, or the like, and comprehensively controls operation of the first treatment device 41 that is connected by the first electrical cable C1 or operation of the second treatment device 42 that is connected by the second electrical cable C2. The generator 43 includes, as illustrated in FIG. 1, a treatment energy output unit 431 and a second processor 432.

The treatment energy output unit 431 supplies, to the first treatment device 41 that is connected by the first electrical cable C1 or the second treatment device 42 that is connected by the second electrical cable C2, electric power that is needed to apply the treatment energy to the target region, under the control of the second processor 432.

For example, if the first treatment device 41 is configured to apply ultrasound energy to the target region, the first treatment device 41 includes an ultrasound transducer that generates ultrasound vibration in accordance with the electric power supplied from the treatment energy output unit 431. Further, one of the first grasper 418 and the second grasper 419 includes a vibration transmission member that transmits the ultrasound vibration, and applies the transmitted ultrasound vibration to the target region that is grasped between the first grasper 418 and the second grasper 419.

Meanwhile, if the second treatment device 42 is configured to apply ultrasound energy to the target region, the second treatment device 42 includes an ultrasound transducer that generates ultrasound vibration in accordance with the electric power supplied from the treatment energy output unit 431. Further, the end effector 423 includes a vibration transmission member that transmits the ultrasound vibration, and applies the transmitted ultrasound vibration to the target region.

Furthermore, for example, if the first treatment device 41 is configured to apply high-frequency energy to the target region, each of the first grasper 418 and the second grasper 419 includes an electrode to which the electric power is supplied from the treatment energy output unit 431. Moreover, if the electric power is supplied to the pair of electrodes, a high-frequency electric current flows into the target region that is grasped between the pair of electrodes.

Meanwhile, if the second treatment device 42 is configured to apply high-frequency energy to the target region, the end effector 423 includes, in a space formed with a counter electrode plate that is attached to a front side of a subject, an electrode to which the electric power is supplied from the treatment energy output unit 431. Further, if the electric power is supplied between the electrode and the counter electrode plate, a high-frequency electric current flows into the target region that is located between the end effector 423 and the counter electrode plate.

Furthermore, for example, if the first treatment device 41 is configured to apply thermal energy to the target region, at least one of the first grasper 418 and the second grasper 419 includes a heater that generates heat in accordance with the electric power supplied from the treatment energy output unit 431. Moreover, at least one of the first grasper 418 and the second grasper 419 transmits the heat of the heater to the target region that is grasped between the first grasper 418 and the second grasper 419 in accordance with the supplied electric power.

Meanwhile, if the second treatment device 42 is configured to apply thermal energy to the target region, the end effector 423 includes a heater that generates heat in accordance with the electric power supplied from the treatment energy output unit 431. Further, the end effector 423 transmits the heat of the heater to the target region in accordance with the supplied electric power.

The second processor 432 is configured with, for example, a CPU, an FPGA, or the like. Further, the second processor 432 performs treatment control in accordance with the first treatment start operation that is performed on the first switch 413 by the operator or the second treatment start operation that is performed on the second switch 422 by the operator. The treatment control is to cause the treatment energy output unit 431 to supply the electric power to the first treatment device 41 or the second treatment device 42, and apply the treatment energy to the target region to perform treatment on the target region.

Control Method Implemented by First Processor

A control method implemented by the first processor 225 will be described below.

Figure 2:
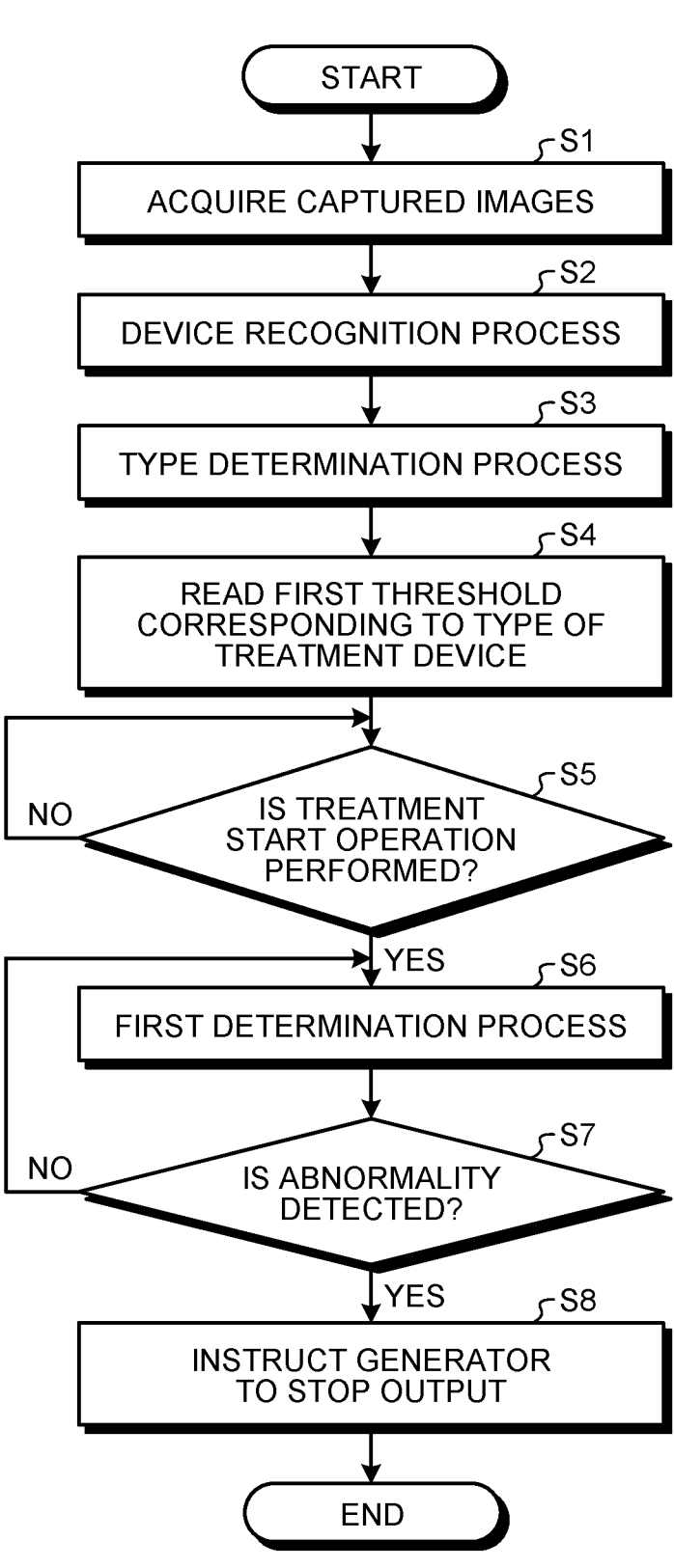
FIG. 2 is a flowchart illustrating a control method implemented by a first processor.

FIG. 2 is a flowchart illustrating the control method implemented by the first processor 225.

Meanwhile, in the following, for convenience of explanation, the first treatment device 41 and the second treatment device 42 are collectively described as a treatment device 40.

Further, the first processor 225 sequentially acquires, in frame units, captured images (digital signals) that are obtained by the imaging unit 213 by capturing images of the inside of the living body and that have passed through the analog processing unit 221, the A/D converter 222, and the image processing unit 223 (Step S1).

Meanwhile, in the first embodiment, at Step S1, the first processor 225 acquires the captured images that are obtained by the imaging unit 213 by capturing images of the inside of the living body and that have passed through the analog processing unit 221, the A/D converter 222, and the image processing unit 223, but embodiments are not limited to this example. For example, at Step S1, the first processor 225 may acquire captured images that are obtained by the imaging unit 213 by capturing images of the inside of the living body and that have passed through the analog processing unit 221 and the A/D converter 222 (the captured images that are not yet subjected to various kinds of image processing by the image processing unit 223).

After Step S1, the first processor 225 performs a device recognition process as described below (Step S2).

Figure 3:
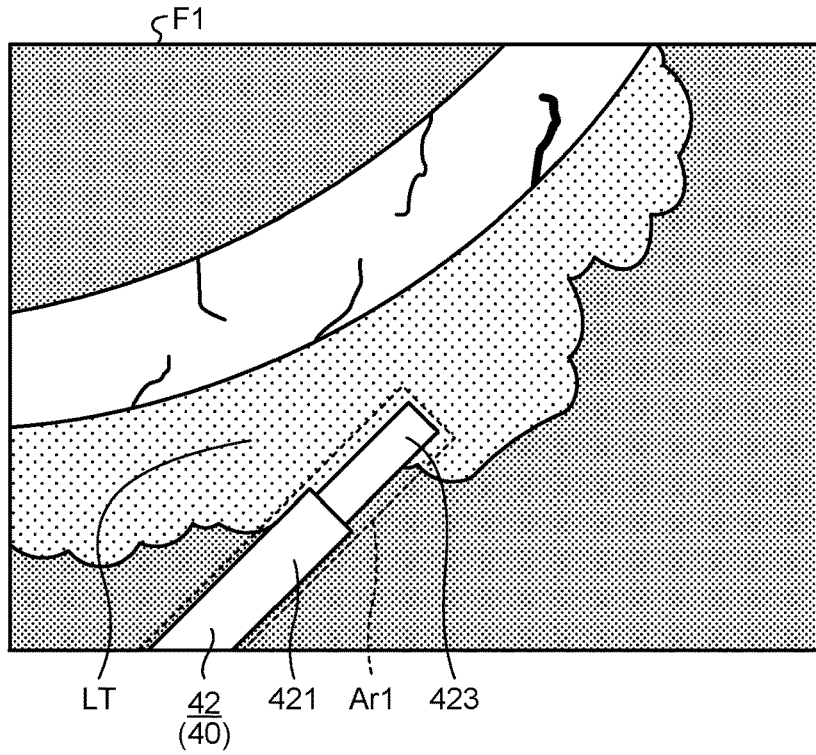
FIG. 3 is a diagram for explaining a device recognition process (Step S2)

FIG. 3 is a diagram for explaining the device recognition process (Step S2). Specifically, FIG. 3 illustrates a captured image F1 that is acquired at Step S1. Meanwhile, in FIG. 3, a case is illustrated in which the second treatment device 42 between the first treatment device 41 and the second treatment device 42 is used.

First, as illustrated in FIG. 3, the first processor 225 extracts a region Ar1 that is formed of pixels with a specific color (for example, silver) that is unique to the treatment device 40 in the captured image F1.

Subsequently, the first processor 225 determines whether the extracted region Ar1 extends in a linear manner from an edge of the captured image F1.

If the first processor 225 determines that the extracted region Ar1 extends in a linear manner from the edge of the captured image F1, the first processor 225 recognizes the region Ar1 as the treatment device 40 (the second treatment device 42 in the case of FIG. 3) that appears in the captured image F1.

Meanwhile, the first processor 225 sequentially performs the device recognition process (Step S2) as described above on the captured images that are sequentially acquired in frame units at Step S1.

After Step S2, the first processor 225 performs a type determination process to be described below (Step S3).

Here, in the memory 226, a clam-type first threshold, a non-clamp type first threshold that is a different value from the clamp-type first threshold, and a learning model to be described below are stored as information that is needed for the process performed by the first processor 225.

The learning model is a model that is provided for each of types of the treatment device 40 (a type of the first treatment device 41 is a clamp-type, and a type of the second treatment device 42 is a non-clamp type), and is obtained by performing machine learning (for example, deep learning or the like) on characteristics of the treatment device 40 on the basis of a captured image (teacher image) that is obtained by capturing an image of the treatment device 40. Further, the first processor 225 is able to determine the type of the treatment device 40 (the type of the first treatment device 41 is a clamp-type, and the type of the second treatment device 42 is a non-clamp type) that appears in the captured image by image recognition using the learning model (image recognition using artificial intelligence (AI)).

Furthermore, the first processor 225 performs the type determination process for determining the type of the treatment device 40 (the type of the first treatment device 41 is a clamp-type, and the type of the second treatment device 42 is a non-clamp type) that appears in the captured images acquired at Step S1, by the image recognition using the learning model stored in the memory 226 (Step S3).

After Step S3, the first processor 225 reads, from the memory 226, the first threshold corresponding to the type of the treatment device 40 that is determined at Step S3 (Step S4). In other words, the first processor 225 reads the clamp-type first threshold from the memory 226 if it is determined that the type of the treatment device 40 is a clamp type, and reads the non-clamp type first threshold from the memory 226 if it is determined that the type of the treatment device 40 is a non-clamp type.

After Step S4, the first processor 225 continuously monitors whether the treatment start operation (the first treatment start operation or the second treatment start operation in the first embodiment) is performed (Step S5). Meanwhile, if the first treatment start operation or the second treatment start operation is performed, the second processor 432 starts the treatment control. In other words, application of the treatment energy from the grasping unit 415 or the end effector 423 to a target region LT (FIG. 3) is started. The second processor 432 outputs a signal indicating that the treatment start operation is performed to the first processor 225 through the third electrical cable C3. With this signal, the first processor 225 determines that the treatment start operation is performed.

If it is determined that the treatment start operation is performed (Step S5: Yes), the first processor 225 performs a first determination process to be described below (Step S6).

Figure 4:
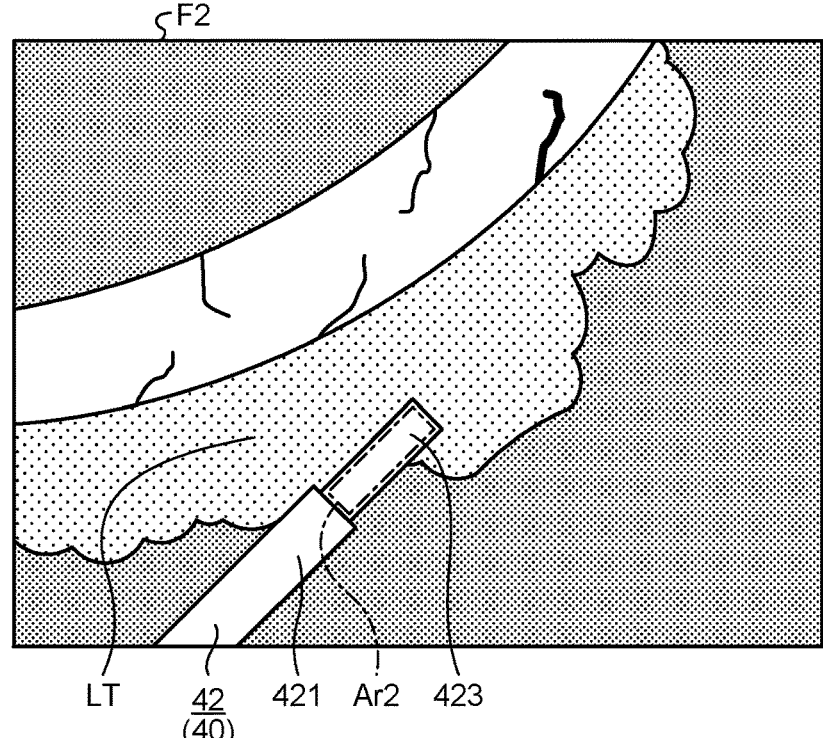
FIG. 4 is a diagram for explaining a first determination process (Step S6)
Figure 5:
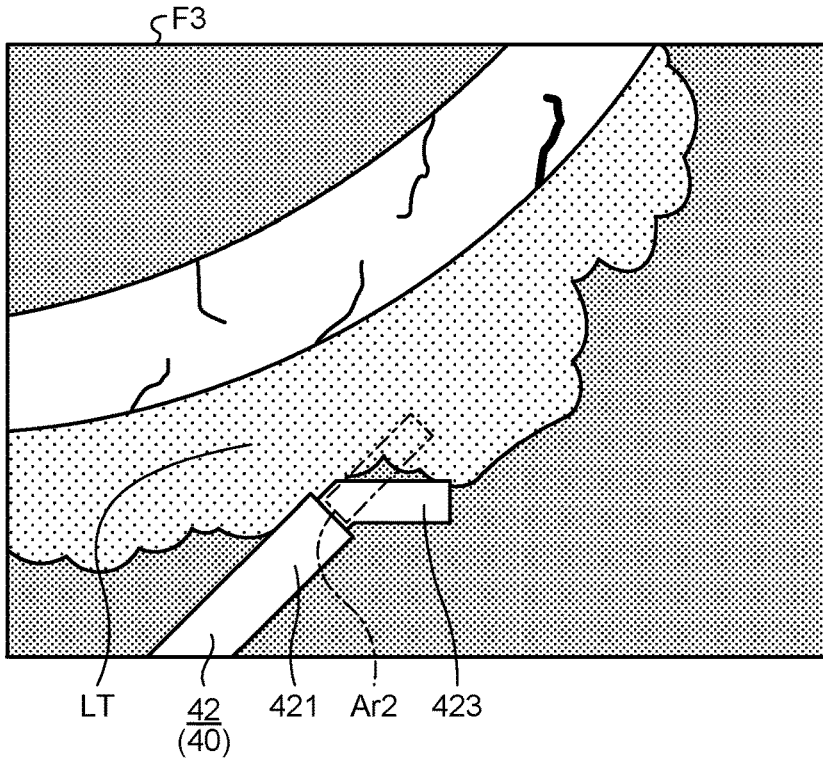
FIG. 5 is a diagram for explaining the first determination process (Step S6)
Figure 6:
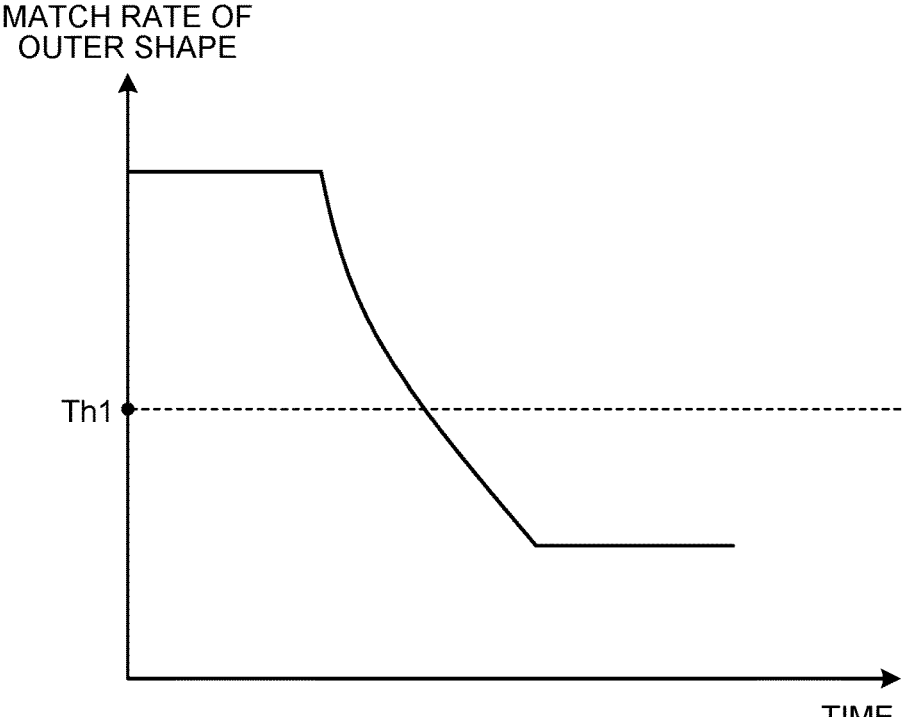
FIG. 6 is a diagram for explaining the first determination process (Step S6)

FIG. 4 to FIG. 6 are diagrams for explaining the first determination process (Step S6). Specifically, FIG. 4 and FIG. 5 illustrate captured images F2 and F3 that are acquired at Step S1. Meanwhile, in FIG. 4 and FIG. 5, a case is illustrated in which the second treatment device 42 between the first treatment device 41 and the second treatment device 42 is used, similarly to FIG. 3. Further, the captured image F2 illustrated in FIG. 4 is an image that is obtained by imaging a state at the time of start of application of the treatment energy to the target region LT. The captured image F3 illustrated in FIG. 5 is an image that is obtained by imaging a state in which the end effector 423 has bent after the start of application of the treatment energy to the target region LT. FIG. 6 is a diagram illustrating a behavior of a match rate of an outer shape of the end effector 423.

First, the first processor 225 extracts a frame Ar2 (FIG. 4) that represents a contour of the outer shape of the end effector 423 (or the grasping unit 415 if the first treatment device 41 is used) on the basis of the captured image F2 that is obtained at the time of the start of application of the treatment energy to the target region LT.

Specifically, the first processor 225 extracts the frame Ar2 as described above by identifying the end effector 423 that is located in the region Ar1 (the treatment device 40) extracted at Step S2, on the basis of a pixel value or characteristics of the shape. Further, the first processor 225 stores the extracted frame Ar2 in the memory 226.

Subsequently, the first processor 225 calculates a match rate of the outer shape of the end effector 423 (or the grasping unit 415 if the first treatment device 41 is used) in the captured image (for example, the captured image F3) of a frame at the present time (hereinafter, described as a current frame) with respect to a specific outer shape (the frame Ar2 stored in the memory 226).

Specifically, the first processor 225 identifies the second holding case 421 (or the shaft 414 if the first treatment device 41 is used) that is located in the region Ar1 (the treatment device 40) extracted at Step S2 in the captured image of the current frame, on the basis of the pixel value or the characteristics of the shape. Further, if linearity of the treatment device 40 is maintained in the captured image of the current frame, the first processor 225 assigns the frame Ar2 stored in the memory 226 to a distal end portion of the identified second holding case 421. Then, the first processor 225 calculates, as the match rate of the outer shape, a rate of the number of pixels with pixel values unique to the end effector 423 (or the grasping unit 415 if the first treatment device 41 is used) in the frame Ar2 with respect to an area (the number of pixels) of the frame Ar2 in the captured image of the current frame. Meanwhile, the first processor 225 sequentially calculates the match rates of the outer shapes in frame units with respect to the captured images that are sequentially acquired at Step S1. The match rate of the outer shape corresponds to a determination value.

Subsequently, the first processor 225 sequentially compares the calculated match rates of the outer shapes and a first threshold Th1 (FIG. 6) that is read at Step S4. Further, if the match rate of the outer shape is equal to or smaller than the first threshold Th1, the first processor 225 determines that an abnormality occurs in the end effector 423 (or the grasping unit 415 if the first treatment device 41 is used) (detects an abnormality).

Meanwhile, if the end effector 423 (or the grasping unit 415 if the first treatment device 41 is used) has bent or fallen off after the bend, the match rate of the outer shape as described above decreases and becomes equal to or smaller than the first threshold Th1. In other words, in the first embodiment, bend or falling off after bend is determined as an abnormality of the end effector 423 (or the grasping unit 415 if the first treatment device 41 is used).

Furthermore, if the abnormality is detected (Step S7: Yes), the first processor 225 instructs the generator 43 (the second processor 432) to stop output, via the third electrical cable C3 (Step S8). Accordingly, the second processor 432 stops supply of the electric power to the treatment device 40 (stops operation of the treatment energy output unit 431).

According to the first embodiment as described above, it is possible to achieve effects as described below.

The control device 22 according to the first embodiment determines whether an abnormality has occurred in the grasping unit 415 or the end effector 423 on the basis of the captured images (for example, the captured images F1 to F3) that are obtained by imaging a state in which the treatment energy is applied to the target region LT from the grasping unit 415 or the end effector 423, and if it is determined that the abnormality has occurred, the control device 22 stops supply of the electric power to the treatment device 40.

In other words, abnormality determination is performed on the basis of the captured images, so that it is possible to detect various abnormalities (bend and falling off after bend in the first embodiment) in the grasping unit 415 or the end effector 423, and it is possible to improve usability.

Furthermore, the control device 22 according to the first embodiment uses the match rate of the outer shape as described above for the abnormality determination (the first determination process (Step S6)), so that it is possible to detect bend or falling off after bend in the grasping unit 415 or the end effector 423 with high accuracy.

Moreover, the control device 22 according to the first embodiment performs the type determination process (Step S3) as described above, so that it is possible to detect the abnormality in the grasping unit 415 or the end effector 423 by using the appropriate first threshold in accordance with the type of the treatment device 40.

Second Embodiment

A second embodiment will be described below.

In the following description, the same components as those of the first embodiment as described above are denoted by the same reference symbols, and detailed explanation thereof will be omitted or simplified.

FIG. 7 is a flowchart illustrating a control method according to the second embodiment.

In the second embodiment, as illustrated in FIG. 7, the control method performed by the first processor 225 is different from that of the first embodiment as described above.

In the control method according to the second embodiment, as illustrated in FIG. 7, Steps S4A, S6A, and S7A are adopted instead of Steps S4, S6, and S7 in the control method (FIG. 2) described above in the first embodiment. Steps S4A, S6A, and S7A will be mainly described below.

Step S4A is performed after Step S3.

In the second embodiment, a second threshold is stored in the memory 226. Further, in the memory 226, a clamp-type third threshold and a non-clamp-type third threshold that is a different value from the clamp-type third threshold are stored instead of the clamp-type first threshold and the non-clamp-type first threshold.

Further, the first processor 225 reads, from the memory 226, the third threshold corresponding to the type of the treatment device 40 determined at Step S3 (Step S4A). In other words, the first processor 225 reads the clamp-type third threshold from the memory 226 if it is determined that the type of the treatment device 40 is a clamp type, and reads the non-clamp type third threshold from the memory 226 if it is determined that the type of the treatment device 40 is a non-clamp type.

Thereafter, the first processor 225 goes to Step S5.

Step S6A is performed if it is determined that the treatment start operation is performed (Step S5: Yes).

Specifically, the first processor 225 performs a second determination process to be described below at Step S6A.

Figure 8:
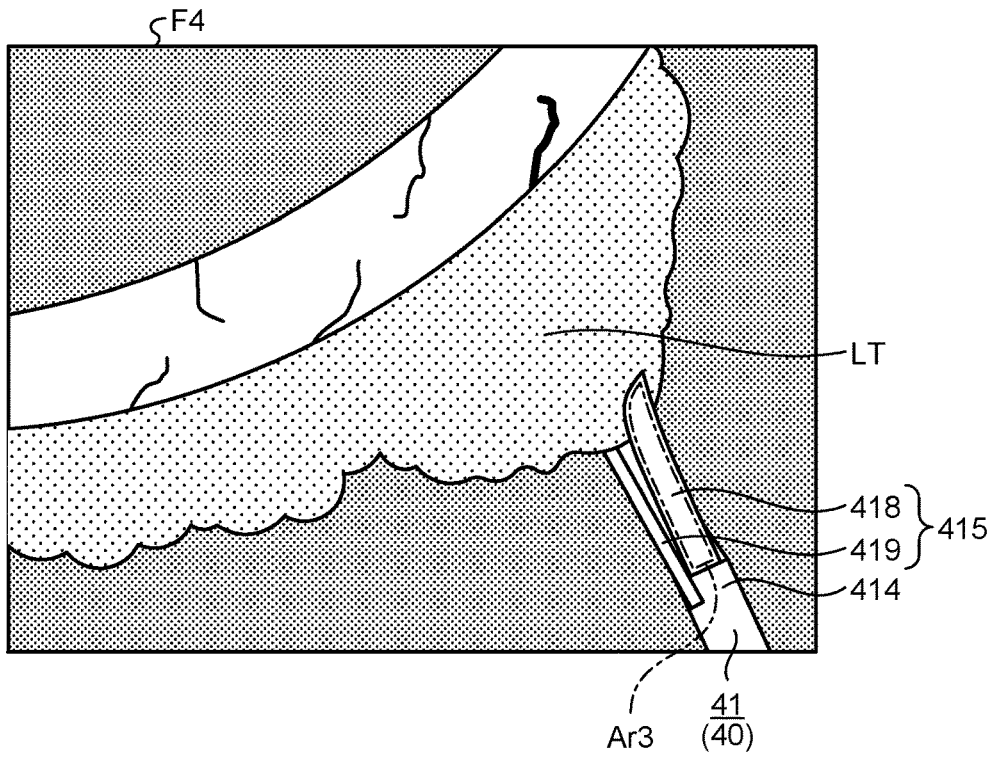
FIG. 8 is a diagram for explaining a second determination process (Step S6A)
Figure 9:
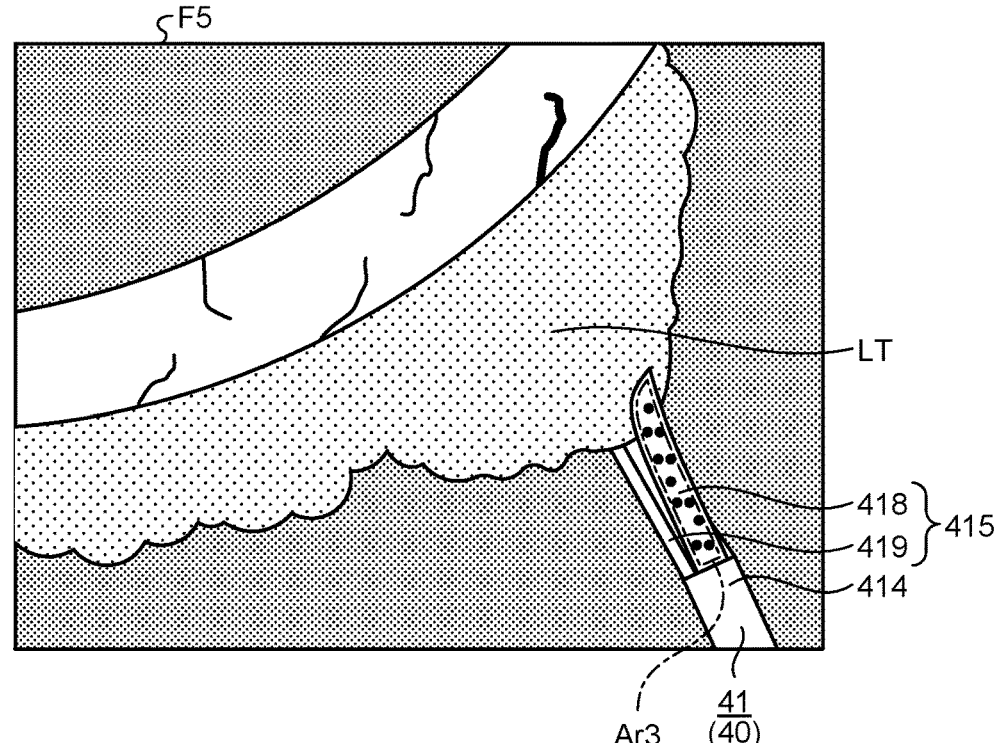
FIG. 9 is a diagram for explaining the second determination process (Step S6A)
Figure 10:
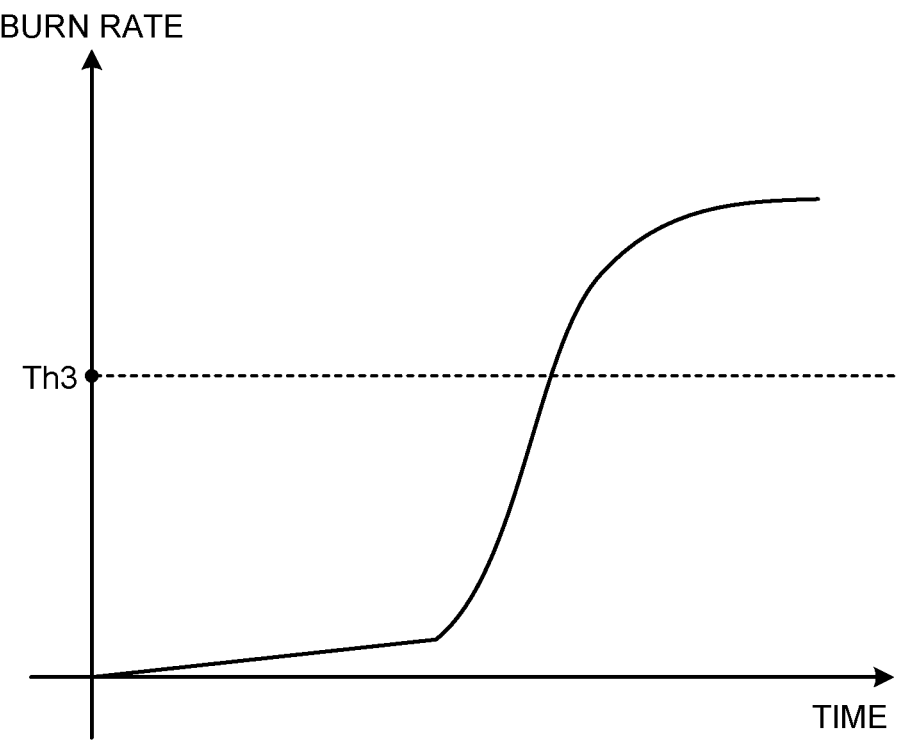
FIG. 10 is a diagram for explaining the second determination process (Step S6A)

FIG. 8 to FIG. 10 are diagrams for explaining the second determination process (Step S6A). Specifically, FIG. 8 and FIG. 9 illustrate captured images F4 and F5 that are acquired at Step S1. Meanwhile, in FIG. 8 and FIG. 9, a case is illustrated in which the second treatment device 42 between the first treatment device 41 and the second treatment device 42 is used. Further, the captured image F4 illustrated in FIG. 8 is an image that is obtained by imaging a state at the time of start of application of the treatment energy to the target region LT. The captured image F5 illustrated in FIG. 9 is an image that is obtained by imaging a state in which the first grasper 418 is burnt after the start of application of the treatment energy to the target region LT. Meanwhile, in FIG. 9, burnt portions are represented by black circles. FIG. 10 is a diagram illustrating a behavior of a burn rate.

First, the first processor 225 identifies the grasping unit 415 (or the end effector 423 if the second treatment device 42 is used) that is located in the region Ar1 (the treatment device 40) extracted at Step S2, on the basis of the pixel value or the characteristics of the shape. Further, the first processor 225 sets a region Ar3 (FIG. 8 and FIG. 9) in the identified grasping unit 415. In the second embodiment, the first processor 225 sets the entire first grasper 418 as the region Ar3. The region Ar3 corresponds to a first region and a specific region. Meanwhile, the first processor 225 sequentially sets the regions Ar3 in frame units in the captured images that are sequentially acquired at Step S1.

Subsequently, the first processor 225 calculates an initial area (the number of pixels) of the set region Ar3 on the basis of the captured image F4 that is obtained obtained at the start of application of the treatment energy to the target region LT. Further, the first processor 225 stores the initial area (the number of pixels) in the memory 226.

Subsequently, the first processor 225 extracts, in the region Ar3, pixels (hereinafter, described as burnt pixels (represented by black circles in FIG. 9)) with pixel values that are equal to or smaller than the second threshold stored in the memory 226, and calculates the number of the burnt pixels. Meanwhile, the first processor 225 sequentially calculates the numbers of the burnt pixels in frame units in the captured images that are sequentially acquired at Step S1.

Subsequently, the first processor 225 calculates a rate (burn rate) of the calculated number of burnt pixels with respect to the initial area (the number of pixels) stored in the memory 226. Meanwhile, the first processor 225 sequentially calculates the burn rates in frame units in the captured images that are sequentially acquired at Step S1. The burn rate corresponds to a determination value.

Subsequently, the first processor 225 sequentially compares the calculated burn rates and the third threshold Th3 (FIG. 10) that is read at Step S4A. Further, if the burn rate is equal to or larger than the third threshold Th3, the first processor 225 determines that the abnormality has occurred in the grasping unit 415 (or the end effector 423 if the second treatment device 42 is used) (detects an abnormality). In other words, in the second embodiment, excessive burn of the grasping unit 415 (or the end effector 423 if the second treatment device 42 is used) is determined as the "abnormality".

Further, if an abnormality is detected (Step S7A: Yes), the first processor 225 goes to Step S8.

According to the second embodiment as described above, it is possible to achieve effects as described below, in addition to the effects of the first embodiment as described above.

The control device 22 according to the second embodiment uses the burn rate as described above for the abnormality determination (the second determination process (Step S6A)), so that it is possible to detect excessive burn of the grasping unit 415 or the end effector 423 with high accuracy.

Third Embodiment

A third embodiment will be described below.

In the following description, the same components as those of the first embodiment as described above are denoted by the same reference symbols, and detailed explanation thereof will be omitted or simplified.

Figure 11:
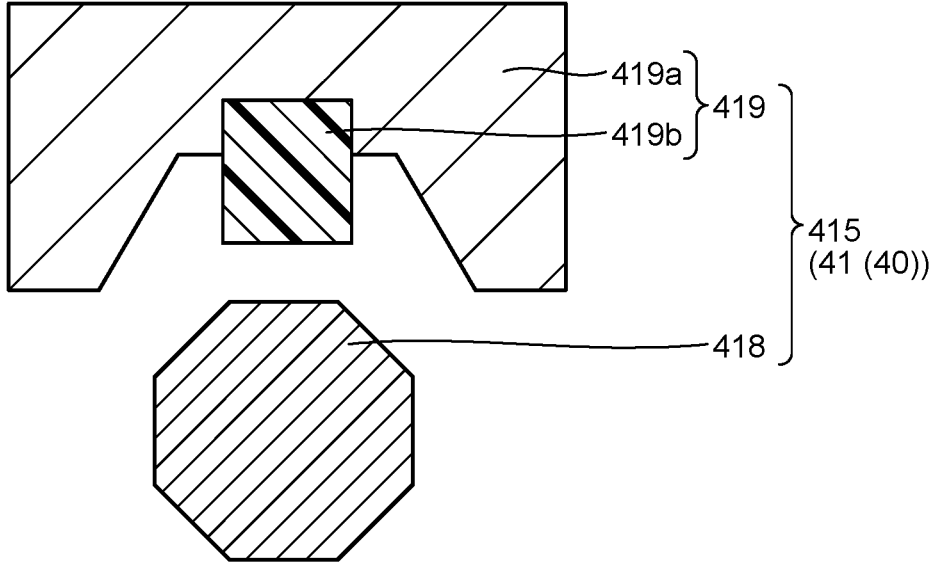
FIG. 11 is a diagram illustrating a configuration of a grasping unit according to a third embodiment.
Figure 12:
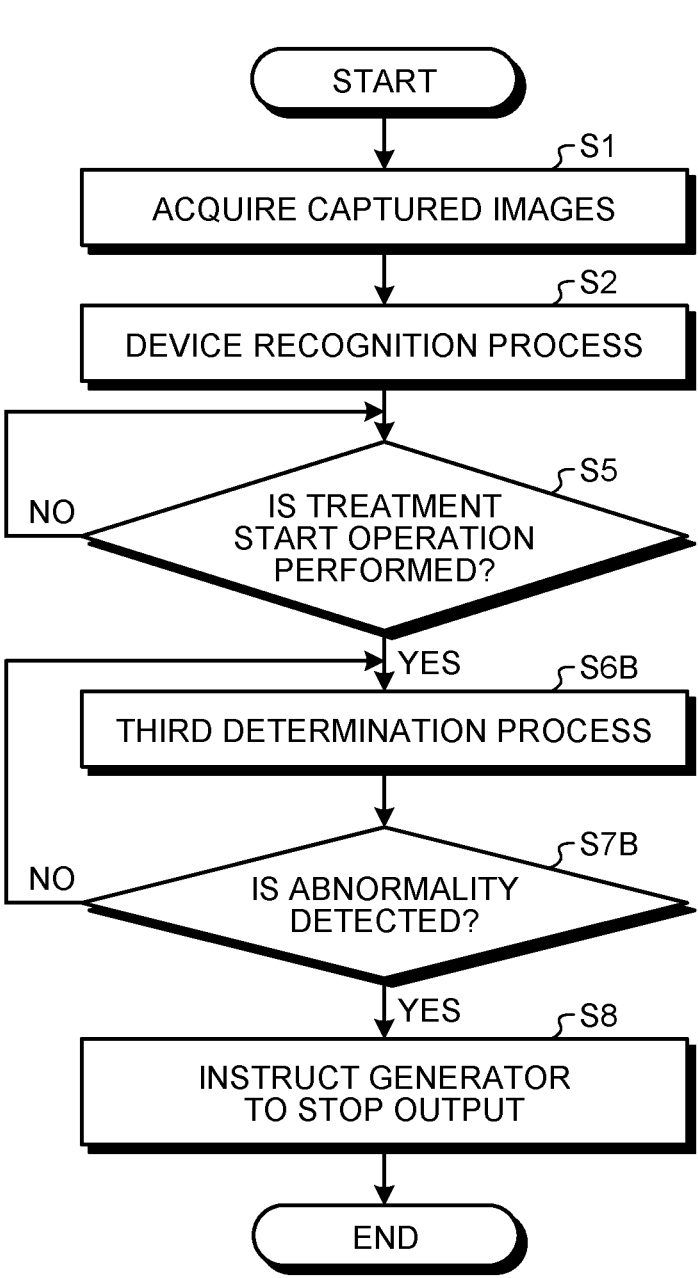
FIG. 12 is a flowchart illustrating a control method according to the third embodiment.

FIG. 11 is a diagram illustrating a configuration of the grasping unit 415 according to the third embodiment. Specifically, FIG. 11 is a cross-sectional view of the grasping unit 415 taken along a plane perpendicular to the central axis Ax1 (FIG. 1). FIG. 12 is a flowchart illustrating a control method according to the third embodiment.

The first processor 225 according to the third embodiment detects an abnormality that may occur in the grasping unit 415 of the clamp-type first treatment device 41 illustrated in FIG. 11. In other words, in the third embodiment, the non-clamp type second treatment device 42 is not a target for the abnormality determination. Further, with this assumption, in the third embodiment, as illustrated in FIG. 12, the control method performed by the first processor 225 is different from that of the first embodiment as described above.

The first treatment device 41 according to the third embodiment is configured to apply ultrasound energy from the first grasper 418 to the target region LT in accordance with the electric power supplied from the treatment energy output unit 431. In other words, the first treatment device 41 includes an ultrasound transducer that generates ultrasound vibration in accordance with the electric power supplied from the treatment energy output unit 431. Further, the first grasper 418 includes a vibration transmission member that transmits the ultrasound vibration. Furthermore, the second grasper 419 includes, as illustrated in FIG. 11, a jaw 419*a* and a resin pad 419*b*.

The jaw 419*a* is opened and closed with respect to the first grasper 418 in accordance with the open-close operation that is performed on the operation knob 412 by the operator.

The resin pad 419*b* is configured with a white resin member, and is mounted on a surface of the jaw 419*a* facing the first grasper 418. The resin pad 419*b* has a function to prevent the first grasper 418 that is generating ultrasound vibration from being broken by hitting against the jaw 419*a* even if incision of the target region LT is completed and the second grasper 419 comes into contact with the first grasper 418.

In the control method according to the third embodiment, as illustrated in FIG. 12, Steps S3 and S4 are omitted and Steps S6B and S7B are adopted instead of Steps S6 and S7 in the control method (FIG. 2) of the first embodiment described above. In the following, Steps S6B and S7B will be mainly described. Meanwhile, in the third embodiment, the first processor 225 goes to Step S5 after Step S2.

In the third embodiment, a fourth threshold is stored in the memory 226. Further, a fifth threshold is stored in the memory 226 instead of the clamp-type first threshold and the non-clamp-type first threshold.

Step S6B is performed if it is determined that the treatment start operation is performed (Step S5: Yes).

Specifically, the first processor 225 performs a third determination process as described below at Step S6B.

Figure 13:
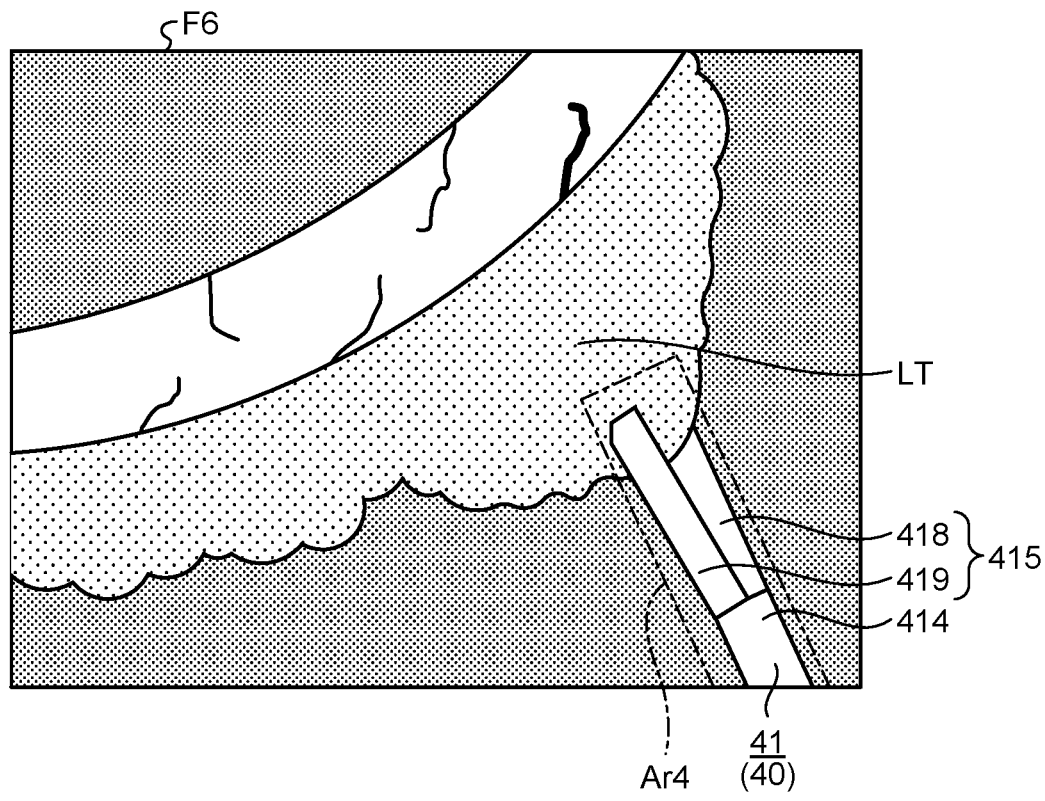
FIG. 13 is a diagram for explaining a third determination process (Step S6B)
Figure 14:
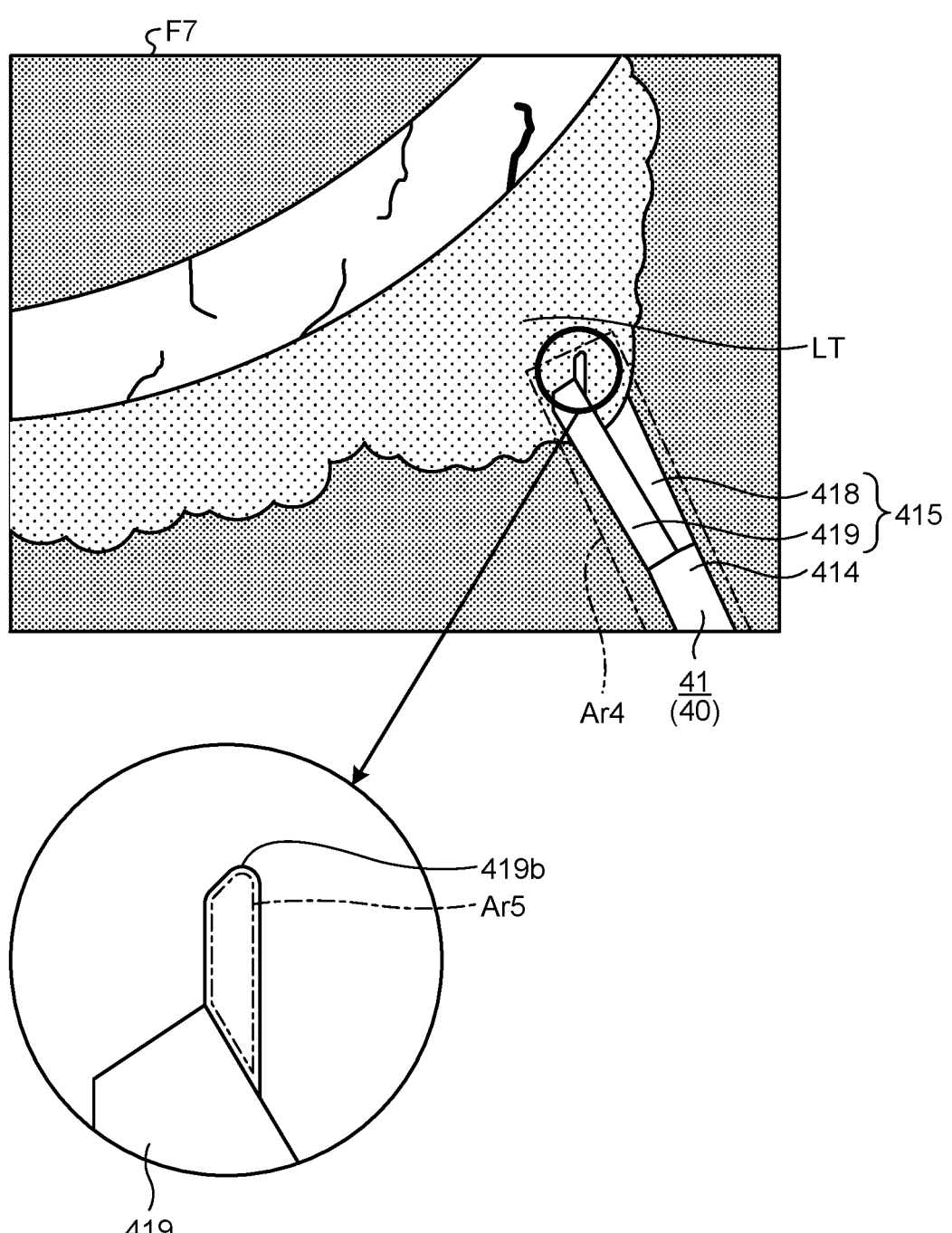
FIG. 14 is a diagram for explaining the third determination process (Step S6B)
Figure 15:
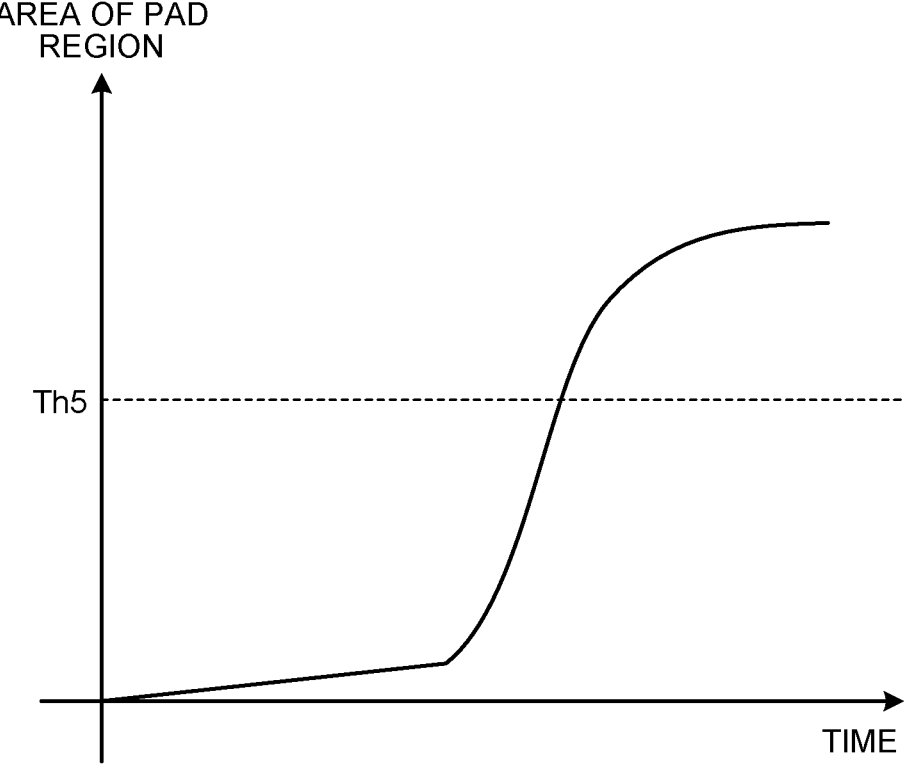
FIG. 15 is a diagram for explaining the third determination process (Step S6B).

FIG. 13 to FIG. 15 are diagrams for explaining the third determination process (Step S6B). Specifically, FIG. 13 and FIG. 14 illustrate captured images F6 and F7 that are acquired at Step S1. Further, the captured image F6 illustrated in FIG. 13 is an image that is obtained by imaging a state at the time of start of application of the treatment energy to the target region LT. The captured image F7 illustrated in FIG. 14 is an image that is obtained imaging a state in which the resin pad 419*b* protrudes after the start of application of the treatment energy to the target region LT. FIG. 15 is a diagram illustrating a behavior of an area of a pad region.

First, the first processor 225 identifies a region Ar4 (FIG. 13 and FIG. 14) including the region Ar1 (the first treatment device 41) extracted at Step S2. Meanwhile, the first processor 225 sequentially identifies the regions Ar4 in frame units in the captured images that are sequentially acquired at Step S1. Each of the regions Ar4 identified in each of the captured images (for example, the captured images F6 and F7) is a region that has the same positional relationship with respect to each of the regions Ar1 (the first treatment device 41) that are extracted in each of the captured images. The region Ar4 corresponds to the first region.

Subsequently, the first processor 225 extracts a pad region Ar5 (FIG. 14) that is formed of pixels with pixel values that are equal to or larger than the fourth threshold stored in the memory 226 in the region Ar4, and calculates an area of the pad region Ar5. Meanwhile, the first processor 225 calculates the areas of the pad regions Ar5 in frame units in the captured images that are sequentially acquired at Step S1.

Subsequently, the first processor 225 sequentially compares the calculated areas of the pad regions Ar5 and a fifth threshold Th5 (FIG. 15) stored in the memory 226. Further, if the area of the pad region Ar5 is equal to or larger than the fifth threshold Th5, the first processor 225 determines that an abnormality has occurred in the grasping unit (detects an abnormality). In other words, in the third embodiment, excessive protrusion of the resin pad 419*b* is determined as the "abnormality".

Furthermore, if the abnormality is detected (Step S7B: Yes), the first processor 225 goes to Step S8.

According to the third embodiment as described above, it is possible to achieve effects as described below in addition to the effects of the first embodiment as described above.

The control device 22 according to the third embodiment uses the area of the pad region Ar5 as described above for the abnormality determination (third determination process (Step S6B)), so that it is possible to detect excessive protrusion of the resin pad 419*b* with high accuracy.

Other Embodiments

While the embodiments of the disclosure have been described above, the disclosure is not limited to only the first to the third embodiments as described above.

In the first and the second embodiments as described above, the generator 43 is commonly used for the first treatment device 41 and the second treatment device 42, but embodiments are not limited to this example, and it may be possible to arrange a different generator for each of the first treatment device 41 and the second treatment device 42.

In the first to the third embodiments as described above, the scope 21 is configured with a flexible endoscope, but embodiments are not limited to this example. It may be possible to adopt a configuration in which a rigid endoscope and a camera head are combined, instead of the scope 21.

In the first to the third embodiments as described above, it may be possible to adopt, as the treatment tool according to the disclosure, a robotics treatment tool that includes a plurality of arms, joint parts that are connected such that the plurality arms can move relative to each other, and a driving system that operates the joint parts to drive the arms (for example, see Japanese Patent No. 4960112).

In the first to the third embodiments as described above, it may be possible to perform the device recognition process (Step S2) by image recognition using a learning model (image recognition using AI), similarly to the type determination process (Step S3).

In first to the third embodiments as described above, it may be possible to cause the second processor 432 to perform the control methods illustrated in FIG. 2, FIG. 7, and FIG. 12. In other words, it may be possible to cause the second processor 432 instead of the first processor 225 to function as the processor according to the disclosure.

In the first to the third embodiments as described above, it may be possible to cause a plurality of processors to perform the control methods illustrated in FIG. 2, FIG. 7, and FIG. 12. In other words, the processor according to the disclosure need not always be configured with a single processor, but may be configured with a plurality of processors.

The first to the third determination processes (Step S6, S6A, and S6B) explained in the first to the third embodiments described above may be combined appropriately.

In the first to the third embodiments as described above, when the abnormality is detected (Step S7, S7A, and S7B: Yes), it may be possible to cause the display device 3 to display information indicating that the abnormality is detected. Further, when causing the display device 3 to display the information, it may be possible to cause a speaker to output the information, or it may be possible to output the information by causing an LED or the like arranged in the control device 22 to turn on or blink.

In the first to the third embodiments as described above, when the abnormality is detected (Step S7, S7A, and S7B: Yes), it may be possible to store information indicating a type of the abnormality (bend or fall off after bend of the grasping unit 415 or the end effector 423, excessive burning, or excessive protrusion of the resin pad 419b) in a memory (not illustrated) arranged in the treatment device 40.

With this configuration, it is possible to achieve effects as described below when the treatment device 40 is re-manufactured. Meanwhile, re-manufacturing of the treatment device 40 indicates that the used treatment device 40 that has been performed treatment on the target region LT is subjected to a certain process, such as disassembly, cleaning, part replacement, re-assembly, and sterilization, is confirmed to have necessary performance or the like, and is made available again.

In other words, a re-manufacturer that performs re-manufacturing is able to recognize a portion in which the abnormality has occurred by checking the information stored in the memory arranged in the treatment device 40, and determine whether to replace the portion or use the portion as it is.

According to the disclosure, it is possible to improve usability.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
a treatment tool configured to perform treatment on a living tissue by applying treatment energy from an end effector to the living tissue in accordance with supplied electric power;
an imaging apparatus configured to capture an image of the living tissue in a state in which the treatment energy is applied from the end effector to the living tissue; and
a control device including a processor configured to control operation of the imaging apparatus, the processor being configured to:
allow an instruction to control supply of the electric power to the treatment tool,
acquire the captured image from the imaging apparatus,
determine whether an abnormality has occurred in the end effector based on the acquired captured image, and
execute an instruction to stop the supply of the electric power to the treatment tool in response to determining that the abnormality has occurred in the end effector.

2. The treatment system according to claim 1, wherein the processor is configured to:
detect at least one of (i) a change in an outer shape of the end effector and (ii) a change in a pixel value in a first region including the end effector, based on the acquired captured image, and
determine whether the abnormality has occurred in the end effector based on the at least one of the change in the outer shape and the change in the pixel value.

3. The treatment system according to claim 2, further comprising:
a memory configured to store a value of a first threshold, wherein the processor is configured to:
calculate a match rate of the outer shape of the end effector with respect to a specific outer shape, based on the acquired captured image, and
determine that the abnormality has occurred in the end effector when the match rate is equal to or smaller than the first threshold.

4. The treatment system according to claim 2, further comprising:
a memory configured to store values of a second threshold and a third threshold, wherein:
the first region is a specific region in the end effector, and
the processor is configured to:
calculate an area of the specific region and an area of an abnormal region formed of pixels with pixel values equal to or smaller than the second threshold in the specific region, based on the acquired captured image, and
determine that the abnormality has occurred in the end effector when a rate of change of the area of the abnormal region with respect to the area of the specific region is equal to or larger than the third threshold.

5. The treatment system according to claim 2, further comprising:
a memory configured to store values of a fourth threshold and a fifth threshold, wherein:
the end effector includes a pair of graspers configured to grasp the living tissue, a first grasper of the pair of graspers is configured to apply ultrasound energy as the treatment energy to the living tissue, a second grasper of the pair of graspers includes a resin pad at a position facing the first grasper of the pair of graspers, and
the processor is configured to:
calculate an area of a pad region of the resin pad formed of pixels with pixel values equal to or larger than the fourth threshold in the first region, based on the acquired captured image, and
determine that the abnormality has occurred in the end effector when the area of the pad region is equal to or larger than the fifth threshold.

6. The treatment system according to claim 1, further comprising:
a memory configured to store values of a plurality of thresholds, wherein;
the processor is configured to:
determine a type of the treatment tool based on the acquired captured image, and
determine whether the abnormality has occurred in the end effector by comparing a threshold corresponding to the type of the treatment among the plurality of thresholds with a determination value for determining occurrence of the abnormality in the end effector.

7. The treatment system according to claim 1, wherein the processor is configured to determine a type of the treatment tool that appears in the acquired captured image, by image recognition using a model that is obtained by performing machine learning on characteristics of the treatment tool.

8. A control device comprising:

a processor configured to control operation of an imaging apparatus, the processor communicating with a treatment tool performing treatment on a living tissue by applying treatment energy from an end effector to the living tissue in accordance with supplied electric power, the processor being configured to:

allow an instruction to control supply of the electric power to the treatment tool, acquire a captured image that is obtained by the imaging apparatus that captures the image of the living tissue in a state in which the treatment energy is applied to the living tissue from the end effector, determine whether an abnormality has occurred in the end effector based on the acquired captured image, and execute an instruction to stop the supply of the electric power to the treatment tool in response to determining that the abnormality has occurred in the end effector.

9. A control method implemented by a processor of a control device, the control method comprising:

acquiring a captured image that is obtained by an imaging apparatus that captures the image of living tissue in a state in which treatment energy is applied from an end effector to the living tissue;

determining whether an abnormality has occurred in the end effector based on the acquired captured image; and executing an instruction to stop supply of electric power to a treatment tool in response to determining that the abnormality has occurred in the end effector.

10. An image determination apparatus comprising:

a processor comprising hardware, the processor being configured to;

allow an instruction to control supply of electric power to a treatment tool, acquire a captured image that is obtained by an imaging apparatus that captures the image of living tissue in a state in which treatment energy is applied from an end effector of the treatment tool to the living tissue, determine whether an abnormality has occurred in the end effector based on the acquired captured image; and execute an instruction to stop the supply of the electric power to the treatment tool in response to determining that the abnormality has occurred in the end effector.

11. The image determination apparatus according to claim 10, wherein the determine whether an abnormality has occurred in the end effector includes: determining whether an increasing in a burnt portion in the end effector has occurred.

12. The image determination apparatus according to claim 11, wherein the determining whether an increase in a burnt portion in the end effector has occurred, which includes: determining the burnt portion in the end effector; calculating an area of the burnt portion; and monitoring a value of the area of the burnt portion.

13. An image determination method comprising:

controlling supply of electric power to a treatment tool;

acquiring a captured image that is obtained by an imaging apparatus that captures the image of living tissue in a state in which treatment energy is applied from an end effector of the treatment tool to the living tissue;

determining whether an abnormality has occurred in the end effector based on the captured image; and executing an instruction to stop the supply of the electric power to the treatment tool in response to determining that the abnormality has occurred in the end effector.

14. The image determination method according to claim 13, wherein the determining whether an abnormality has occurred in the end effector includes: determining whether an increase of a burnt portion has occurred in the end effector.

15. The image determination method according to claim 14, wherein the determining whether an increase of the burnt portion has occurred in the end effector includes: determining the burnt portion in the end effector; calculating an area of the burnt portion; and monitoring a value of the area of the burnt portion.

16. The image determination method according to claim 15, wherein the calculate the area of the burnt portion includes: calculating a number of pixels of the burnt portion.

\* \* \* \* \*